(12) United States Patent
Marchosky

(10) Patent No.: US 8,563,040 B2
(45) Date of Patent: *Oct. 22, 2013

(54) COMPOSITIONS AND METHODS FOR FORMING AND STRENGTHENING BONE

(75) Inventor: J. Alexander Marchosky, St. Louis, MO (US)

(73) Assignee: Marfly 2, LP, St. Louis, MO (US)

( * ) Notice: Subject to any disclaimer, the term of this patent is extended or adjusted under 35 U.S.C. 154(b) by 901 days.

This patent is subject to a terminal disclaimer.

(21) Appl. No.: 12/581,467

(22) Filed: Oct. 19, 2009

(65) Prior Publication Data

US 2010/0136120 A1  Jun. 3, 2010

Related U.S. Application Data

(63) Continuation of application No. 10/071,490, filed on Feb. 7, 2002, now abandoned.

(51) Int. Cl.
| | |
|---|---|
| A61K 9/14 | (2006.01) |
| A61K 35/32 | (2006.01) |
| A61K 33/00 | (2006.01) |
| A61K 35/12 | (2006.01) |
| A61K 45/00 | (2006.01) |
| A61K 38/12 | (2006.01) |
| A61F 13/00 | (2006.01) |

(52) U.S. Cl.
USPC ........... 424/488; 424/489; 424/422; 424/549; 424/600; 424/572; 424/85.2; 514/21.1

(58) Field of Classification Search
USPC ......... 424/488, 489, 422, 421, 549, 602, 572, 424/85.2, 94.6, 600; 514/21, 801, 21.1; 623/919
See application file for complete search history.

(56) References Cited

U.S. PATENT DOCUMENTS

| | | |
|---|---|---|
| 414,973 A | 2/1979 | Balazs |
| 4,440,750 A | 4/1984 | Glowacki et al. |
| 4,642,120 A | 2/1987 | Nevo et al. |
| 4,837,379 A | 6/1989 | Weinberg |
| 5,073,373 A | 12/1991 | O'Leary et al. |
| 5,166,331 A | 11/1992 | della Valle et al. |
| 5,314,476 A | 5/1994 | Prewett et al. |
| 5,356,629 A | 10/1994 | Sander et al. |
| 5,457,093 A | 10/1995 | Cini et al. |
| 5,563,124 A | 10/1996 | Damien et al. |
| 5,629,287 A | 5/1997 | Brown et al. |
| 5,645,591 A | 7/1997 | Kuberasampath et al. |
| 5,685,716 A | 11/1997 | Linkow |
| 5,702,716 A | 12/1997 | Dunn et al. |
| 5,705,485 A | 1/1998 | Cini et al. |
| 5,711,957 A | 1/1998 | Patat et al. |
| 5,755,792 A | 5/1998 | Brekke |
| 5,776,193 A | 7/1998 | Kwan et al. |
| 5,786,327 A | 7/1998 | Tam |
| 5,830,493 A * | 11/1998 | Yokota et al. .................. 424/426 |
| 5,837,258 A | 11/1998 | Grotendorst |
| 5,894,070 A | 4/1999 | Hansson et al. |
| 5,916,870 A | 6/1999 | Lee et al. |
| 5,942,499 A | 8/1999 | Radomsky |
| 5,948,428 A | 9/1999 | Lee et al. |
| 5,958,441 A | 9/1999 | Oppermann et al. |
| 6,017,940 A | 1/2000 | Petrie et al. |
| 6,030,635 A | 2/2000 | Gertzman et al. |
| 6,049,026 A * | 4/2000 | Muschler .................... 424/93.7 |
| 6,165,487 A | 12/2000 | Ashkar et al. |
| 6,171,610 B1 | 1/2001 | Vacanti et al. |
| 6,214,048 B1 | 4/2001 | Ito et al. |
| 6,372,257 B1 * | 4/2002 | Marchosky ................... 424/488 |
| 6,437,018 B1 | 8/2002 | Gertzman et al. |
| 6,458,375 B1 | 10/2002 | Gertzman et al. |
| RE38,522 E | 5/2004 | Gertzman et al. |
| 6,911,212 B2 | 6/2005 | Gertzman et al. |

FOREIGN PATENT DOCUMENTS

| | | |
|---|---|---|
| DE | 4216496 | 11/1993 |
| EP | 0147021 | 7/1985 |
| EP | 0312208 | 4/1989 |
| EP | 0329239 | 8/1989 |
| EP | 0522569 | 1/1993 |
| EP | 0530804 | 3/1993 |
| EP | 754466 | 1/1997 |
| JP | 63181770 | 7/1988 |
| JP | 01032371 | 2/1989 |
| JP | 01288269 | 11/1989 |
| JP | 05123390 | 5/1993 |
| JP | 05277174 | 10/1993 |
| VU | WO 95/13767 | 5/1995 |
| WO | WO 91/01720 | 2/1991 |
| WO | WO 91/18558 | 12/1991 |
| WO | WO 92/13565 | 8/1992 |

(Continued)

OTHER PUBLICATIONS

Abe et al., "Model-Based Surgical Planning and Simulation of Cranial Base Surgery," (1998) Neurologia Medico-Chirurgica, vol. 38, pp. 746-751.

(Continued)

Primary Examiner — Blessing Fubara
(74) Attorney, Agent, or Firm — Woodard, Emhardt, Moriarty, McNett & Henry LLP

(57) ABSTRACT

Compositions are provided which stimulate bone growth. Also provided are methods for utilizing the compositions for filling in bone defects, promoting rapid fusion of bone fractures, grafts, and bone-prostheses, and promoting strengthening of osteoporotic bones.

15 Claims, 6 Drawing Sheets

(56) References Cited

FOREIGN PATENT DOCUMENTS

| WO | WO 93/00050 | 1/1993 |
|---|---|---|
| WO | WO 93/20858 | 10/1993 |
| WO | WO 94/15653 | 7/1994 |
| WO | WO 96/39203 | 12/1996 |
| WO | WO 97/14376 | 4/1997 |
| WO | WO 97/18842 WO | 5/1997 |
| WO | WO 97/32591 | 4/1998 |
| WO | WO 98/14222 WO | 4/1998 |
| WO | WO 98/22114 | 5/1998 |
| WO | WO 98/40113 | 9/1998 |
| WO | WO 98/56433 | 12/1998 |
| WO | WO 00/45870 | 8/2000 |

OTHER PUBLICATIONS

AU 57799/00 Australian Office Action and Notice of Allowance; May 28, 2004; Jun. 10, 2005.

Bodmeier et al., "Preparation and Evaluation of Drug-Containing Chitosan Beads," (1989) Drug Development Industrial Pharmacy, vol. 15, pp. 1475-1494.

Bruder et al., "Bone Regeneration by Implantation of Purified, Culture-Expanded Human Mesenchymal Stem Cells," (1998) Journal of Orthopaedic Research, vol. 16, pp. 156-162.

Chandy et al., "Chitosan—As a Biomaterial," (1990) Biomat. Art. Cells. Art. Org., vol. 18, pp. 1-24.

Elcin et al., "Neural tissue engineering: Adrenal chromaffin cell attachment and viability on chitosan scaffolds," (1998) Neurological Research, vol. 20, pp. 648-654.

EP 00943009 Annex European Search Report and Supplements, Nov. 6, 2003; Jul. 23, 2003; Apr. 16, 2003.

Epply et al., "Free Bone Graft Reconstruction of Irradiated Facial Tissue: Experimental Effects of Basic Fibroblast Growth Factor Stimulation," (1991) Plastic and Reconstruction Surgery, vol. 88, pp. 1-11.

Gaserod et al., "Microcapsules of alginate-chitosan—I quantitive study of the interaction between alginate and chitosan," (1998) Biomaterials, vol. 19, pp. 1815-1825.

Ibbewhite et al., "Transforming Growth Factor-β Accelerates Osteoinduction in a Craniofacial Only Model,"(1993) Growth Factors, vol. 9, pp. 185-193.

Jameela et al., "Glutaraldehyde cross-linked chitosan microspheres as a long acting biodegradable drug delivery vehicle: studies on the in vitro release of mitoxantrone and in vivo degradation of microspheres in rat muscle," (1995) Biomaterials, vol. 16, pp. 769-775.

Katz et al., "Quantification of holographic fringe data: comparison of intact and implanted femurs," (1998) Medical Engineering & Physics, vol. 20, pp. 114-123.

Klokkevold et al., "Osteogenesis Enhanced by Chitosan (Poly-N-Acetyl Glucosaminoglycan) in Vitro," (1996) J. Periodontol., vol. 67, pp. 1170-1175.

Ko.K, "Superimposed holographic image-guided neurosurgery," (1998) J. Neurosurg., vol. 88, pp. 777-781.

Kyocera Corp., JP 08 182753 A. 1996. Abstract No. XP-002230934. Derwent Publications Ltd., London, United Kingdom.

Miyazaki et al., "Thermally reversible xyloglucan gels as vehicles for rectal drug delivery," (1998) Journal of Controlled Release, vol. 56, pp. 75-83.

Mori et al., "Effects of chitin and its derivatives on the proliferation and cytokine production of fibroblasts in.vitro," (1997) Biomaterials, vol. 8, pp. 947-951.

Mundy et al., "Stimulation of Bone Formation in Vitro and in Rodents by Statins," (1999) Science, vol. 286, No. 5446, pp. 1946-1949.

PCT/US00/17955 International Search Report; Oct. 3, 2000.

PCT/US98/04904 International Search Report, Aug. 7, 1998.

Phillips et al., "Do Growth Factors Stimulate Angiogenesis? A Comparison of Putative Angiogenesis Factors," (1997) Wounds, vol. 9, pp. 1-14.

Pilloni, "The Effect of Hyaluronan on Mouse Intramembranous Osteogenesis in Vitro, " (1997).

Radomsky et al., "Potential Role of Fibroblast Growth Factor in Enhancement of Fracture Healing," (1998) Clinical Orthopaedics and Related Research, No. 355S. pp. S283-298.

Rao et al., "Use of chitosan as a biomaterial: Studies on its safety and hemostatic potential," (1997) Journal of Biomedical Materials Research, vol. 34, pp. 21-28.

Sasaki et al., "Stimulation of Osteoinduction in Bone Wound Healing by High-Molecular Hyaluronic Acid," (1995) Bone, vol. 16, No. 1, pp. 9-15.

Solheim, "Osteoinduction by demineralised bone," (1998) International Orthopaedics, vol. 22, pp. 335-342.

Tabata et al., "Bone regeneration of basic fibroblast growth factor complexed with biodgradable hydrogels," (1998) Biomaterials, vol. 19, pp. 807-815.

Thomson et al., "Fabrication of biodegradable polymer scaffolds to engineer trabecula bone," (1995) J. Biomater. Sci. Polymer Edn., vol. 7, pp. 23-38.

Toa Nenryo Kogyo KK. JP 01 034372 A. 1989. Abstract No. XP-002230935. Derwent Publications Ltd., London, United Kingdom.

Zentner et al., "A holographic study of variations in bone deformations resulting from different headgear forces in a macerated human skull," (1996) The Angle Orthodontist, vol. 66, pp. 463-472.

* cited by examiner

ANT. LATERAL APPROACH TO FEMUR

EXPOSED FEMUR

PLACEMENT OF FIXATOR PLATE

CREATION OF GAP DEFECT

POST-IMPLANTATION OF BONE ALLOGRAFT

MIGRATION OF BONE ALLOGRAFT IN ALGINATE (-Ca 2+)

BONE ALLOGRAFT IS RETAINED WITH ADDITION OF Ca2+

12 WK UNFILLED DEFECT

12 WK ALGINATE CARRIER ALONE

12 WK DBM IN HA+VEGF

12 WK DBM IN HA + VEGF

COMPOSITIONS AND METHODS FOR FORMING AND STRENGTHENING BONE

REFERENCE TO RELATED APPLICATIONS

This application is a continuation of U.S. application Ser. No. 10/071,490, filed Feb. 7, 2002, now abandoned which claims priority from U.S. application Ser. No. 09/606,768, filed Jun. 29, 2000, now U.S. Pat. No. 6,372,257, which claims the benefit of U.S. provisional application Ser. No. 60/141,386 filed on Jun. 29, 1999, and claims the benefit of U.S. application Ser. No. 09/377,283 filed Mar. 30, 1999, now U.S. Pat. No. 6,413,278, which claims the benefit of and is a complete application based upon U.S. Provisional application Ser. No. 60/135,095, filed Mar. 30, 1998, which was converted from a non-provisional application Ser. No. 09/050,498 filed Mar. 30, 1998, now abandoned. All of these applications are hereby incorporated by reference in their entirety.

BACKGROUND OF THE INVENTION

1. Field of the Invention

The present invention generally relates to methods and compositions which promote the controlled and programmable growth and strengthening of bone.

2. Description of Related Art

Various bone diseases, injuries, or surgical interventions in humans and other vertebrates result in bone defects or fractures. Bone growth or restitution is often desired to alleviate these conditions. The bone growth may be desired in areas where bone previously existed and is partially or completely absent, or where its continuity has been disrupted. Situations where such regeneration of bone is necessary or desirable include the healing of fractures, or increasing the bone mass in osteoporotic bones. Bone growth may also be desired in areas where bone did not previously exist. Such bone generation is desirable, e.g., for filling defects, such as caused by removal of tumors or intervertebral discs, for correcting congenital deformities such as cleft palates, or for forming a strong connection between a prosthesis such as a joint replacement and an adjacent bone.

Various compositions are known which are designed to encourage bone growth. These compositions are generally applied to bone defects or fractures to provide an osteoinductive and osteoconductive environment. Examples include those disclosed in U.S. Pat. Nos. 5,563,124; 4,642,120; 5,755,792; 5,830,493; and 5,711,957; PCT Patent Publications WO 94/15653; WO 95/13767; WO 98/56433; and WO 97/32591; and European Patent EP 754,466. Additionally, such compositions are available commercially, including demineralized bone matrix compositions such as Grafton® (Osteotech, Eatontown, N.J.). These compositions generally comprise a porous solid, semisolid, paste or gel material including materials such as gelatin, hyaluronic acid, collagen, amylopectin, demineralized bone matrix, and/or calcium carbonate, to create an osteoconductive environment. The compositions also often include osteoinductive growth factors such as transforming growth factor-13, bone morphogenic protein, or basic fibroblast growth factor. It may be noted that combinations of chitosan with demineralized bone matrix and/or ground or chipped cancellous bone are unknown. Methods for filling bone defects utilizing compositions constituted solely of chitin or chitosan are also unknown.

In spite of the availability of numerous compositions to encourage bone growth, problems still occur in attempts to achieve satisfactory growth of bone to fill bone defects, connect prostheses to existing bone, and fuse fractures and bone grafts to existing bone. Therefore, there is an ongoing need for new compositions to provide alternatives to existing compositions for encouraging bone growth.

SUMMARY OF THE INVENTION

Among the several objects of the present invention may be noted the provision of compositions which promote bone formation and growth. A more specific object of the invention is the provision of compositions which stimulate bone formation and growth through the stimulation of angiogenesis and osteogenesis. Another object of the invention is the provision of methods for stimulating bone formation and growth through the use of angiogenesis-stimulating compositions.

Briefly, therefore, the present invention is directed to a composition comprising the following components: (a) one or more materials selected from the group consisting of fibroblast growth factors, vascular endothelial growth factors, endothelial cell growth factors, transforming growth factors, chitosan, bone, platelet derived endothelial growth factors, placental growth factors, angiogenin, interleukin-8, granulocyte colony-stimulating growth factor, and supernatant fluid from a culture of cells known to produce angiogenic factors; (b) a material comprising demineralized bone matrix, non-decalcified bone matrix, with or without hyaluronic acid; (c) a scaffolding material selected from the group consisting of cancellous bone, chitosan, chitosan-protein, and chitin-protein fibers; and (d) a gel material selected from the group consisting of chitosan, imidazolyl chitosan, methylpyrrolidinone chitosan, carbodiimide chitosan, glutaraldehyde chitosan, alginate, a mixture of alginate with chitosan or a chitosan derivative, hyaluronic acid, and a mixture of hyaluronic acid with chitosan or a chitosan derivative.

Additionally, the present invention is directed to a composition comprising the following components: (a) one or more angiogenesis-stimulating materials; (b) an osteoinductive material; (c) a scaffolding material; and (d) a gel material.

Moreover, the present invention is directed to a composition comprising the following components: (a) one or more angiogenesis-stimulating materials selected from the group consisting of fibroblast growth factors, vascular endothelial growth factors, endothelial cell growth factors, transforming growth factors, chitosan, bone, platelet derived endothelial growth factors, placental growth factors, angiogenin, interleukin-8, granulocyte colony-stimulating growth factor, and supernatant from cells known to produce angiogenic factors; (b) an osteoinductive material comprising demineralized bone matrix, non-decalcified bone matrix, with or without hyaluronic acid; (c) a scaffolding material selected from the group consisting of cancellous bone, chitosan, chitosan-protein, and chitin-protein fibers; and (d) a gel material selected from the group consisting of chitosan, imidazolyl chitosan, methylpyrrolidinone chitosan, carbodiimide chitosan, glutaraldehyde chitosan, alginate, and a mixture of alginate with chitosan or a chitosan derivative.

Furthermore, the present invention is directed to a composition for promoting the growth and strengthening of bone comprising a mixture of chitosan or chitosan derivative, cancellous bone, and demineralized bone matrix. The present invention is also directed to a composition for promoting growth and strengthening of bone comprising a mixture of alginate, calcium, cancellous bone, and demineralized bone matrix. Also, the present invention is directed to a composition for promoting growth and strengthening of bone comprising a mixture of chitosan or chitosan derivative, alginate, cancellous bone, and demineralized bone matrix. Additionally, the present invention is directed to a composition for promoting growth and strengthening of bone comprising a mixture of hyaluronic acid, cancellous bone, and demineralized bone matrix.

The present invention is also directed to a method of inducing bone formation in a vertebrate. The method comprises applying the compositions described above to a site in the vertebrate where bone formation is desired.

In an additional embodiment, the present invention is directed to a method of filling a bone defect. The method comprises filling the bone defect with a rigid material consisting essentially of chitin or chitosan.

DESCRIPTION OF THE FIGURES

FIG. 4A shows the unfilled bone defect of the femur of an athymic nude rat at 12 weeks post defect formation.

FIG. 4B shows the bone defect of the femur of an athymic nude rat filled with alginate carrier alone at 12 weeks post defect implantation of alginate carrier.

DETAILED DESCRIPTION OF THE INVENTION

Figure 1A:
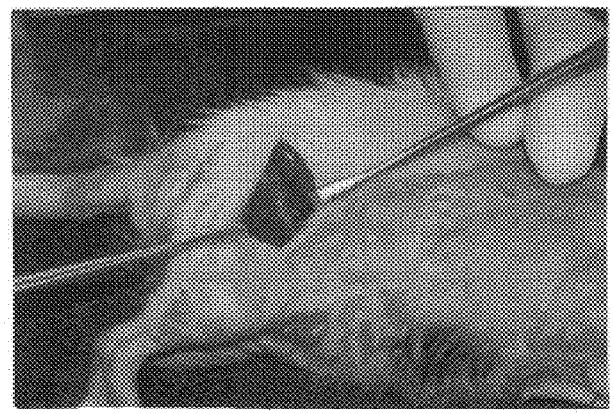
FIG. 1A shows the surgical anterolateral approach to the athymic nude rat models used for study of the bone allograft compositions of this invention as discussed in Example 1.

As used herein, the term "cancellous bone" refers to the medullary portion of bone, devoid of hematogenous and other cellular material. Cancellous bone is generally derived from human or animal cadavers.

The term "demineralized bone matrix" ("DBM") refers to ground cortical bone which has been demineralized. Demineralization is generally achieved by treating the ground bone with acid, usually 0.6N hydrochloric acid. The cortical bone may be obtained from any source, including human or animal cadavers. DBM is known to contain osteoinductive growth factors.

The term "non-decalcified bone matrix" ("NBM") refers to ground cortical bone which has not been demineralized. NBM is known to contain osteoinductive growth factors.

The term "osteoconductive" refers to materials which provide a environment for ingrowth and orientation of osteogenic cells from surrounding tissues. Such materials are generally porous materials, i.e., providing latticework structures similar to cancellous bone.

The term "osteogenic" refers to the process of forming new bone. This formation requires signaling, modulating, and transforming molecules.

The term "osteoinductive" refers to the ability of a material to induce the production of osteoblasts from precursor cells, in particular mesenchymal stem cells. The osteoinductive material may act directly as a growth factor which interacts with precursor cells to induce the osteoblast differentiation, or the material may act indirectly by inducing the production of osteoinductive growth factors. This induction also requires signaling, modulating, and transforming molecules.

When used herein, the term "biocompatible" refers to materials which, when incorporated into the invention composition, have low toxicity, acceptable foreign body reactions in the living body, and affinity with living tissues.

"Chitin" is poly(1,4)$_2$-amino-2-deoxy-$\beta$-D-glucan. It is an abundant polysaccharide which forms, e.g., the structural component of the cell walls of many fungi and the shells of insects and shellfish.

"Chitosan" is N-deacetylated chitin. Deacetylation is generally accomplished by treatment of chitin with alkali such as sodium hydroxide. The degree of N-deacetylation can be controlled by controlling the amount of alkali treatment and time of exposure. The length of the chitosan polysaccharide can also be decreased by degrading the high molecular weight molecule with, e.g., 1 N hydrochloric acid, or by enzymatic treatment. Chitosan in acidic solutions forms gels at concentrations as low as 1% (w/w in 1% v/v acetic acid) (Bodmeier et al., 1989, Drug Devel. & Ind. Pharmacy 15:1475) and is insoluble at pH>6.5. Chitin and chitosan can be cross-linked with charged radicals (i.e. glutaraldehyde, carbodiimide, lysine, vinyl, etc.) to obtain strongly bonded polymers that can be formed into solid or tubular structures. For information on various other characteristics and useful manipulations of chitosan, see, e.g., PCT patent publication WO 98/22114, which is herein incorporated by reference.

No particular form of chitin or chitosan is to be regarded as necessarily more useful than any other form for use in the present invention. The skilled artisan would be able to discern without undue experimentation whether a particular form of chitosan is useful for the particular composition desired.

"Alginate" is a copolymer of (1,4)-$\alpha$-L-guluronic acid and $\beta$-D-mannuronic acid produced by brown algae. A gel is formed when a 2% alginate solution interacts with divalent cations such as calcium. See Gaserod et al., 1998, Biomaterials 19:1815 for additional information on characteristics of alginate.

The term "1 to n", when used with the name of a growth factor, means that various forms of the growth factor, both known and not yet discovered, are intended to be included.

The contents of each of the references cited herein are herein incorporated by reference.

The present invention provides compositions and methods which stimulate bone formation and growth in a vertebrate. These methods are particularly useful for stimulating bone formation in humans and other mammals. The compositions are designed utilizing the unappreciated concept that angiogenesis is a pivotal and crucial factor for inducing bone formation and growth. Thus, angiogenesis-stimulating factors such as vascular endothelial growth factors, platelet derived endothelial cell growth factors, basic fibroblast growth factors, and interleukin-8, or materials which are known to stimulate the production of angiogenesis-stimulating factors (e.g., chitosan) are components which are as important as osteoinductive and osteoconductive factors in the compositions of the present invention.

The compositions of the invention comprise these components: a source of an angiogenesis-stimulating agent, a source of an osteoinductive agent, an osteoconductive scaffolding component, a substance for allowing easy flow and volumetric conformation and for holding the angiogenesis-stimulating agent and osteoinductive agent and allowing the slow release of these components, and a substance for preventing the composition from moving away from the location where placed. It is to be noted that some materials which may be used in the compositions of the present invention may serve as more than one of the above components. Also, the materials of this invention may stimulate bone growth and formation by other or additional mechanisms. The invention compositions may also include materials which are not yet known, but which provide characteristics relating to these components which are similar to the materials described herein.

When a composition of the present invention is placed in a location where bone formation and/or growth is desired, the components of the composition work together to achieve the desired purpose. The angiogenesis-stimulating agent stimulates the growth of neovasculature from existing host tissue, which is vital for the process of new bone formation. The osteoinductive component induces the formation of bone-forming osteoblasts from precursor cells, in particular mesenchymal cells. The material holding and allowing slow release of the angiogenic and osteogenic components assures a release of these growth factors from the composition over a substantial period of the bone forming and growth processes. Where desired, this material will impart characteristics of the composition which allows easy flow, permitting the composition to volumetrically fill the desired space and configuration to deliver the growth factors to their site of action. This filling action also serves to interfere with the ingrowth of fibrous scar-forming tissue and other tissues which could create defects, voids, etc. that may interfere with proper bone formation. The bone which does form around such ingrown tissue may be weak, permitting fractures and failures. The material preventing movement of the composition assures that the composition does not move outside of the intended site. Such movement could reduce the effectiveness of the composition and could be injurious at a site where bone growth is not wanted.

Any known angiogenesis-stimulating agent is useful in the compositions of the present invention. Examples of such agents are individual growth factors known to induce angiogenesis, such as various fibroblast growth factors, various vascular endothelial growth factors, endothelial cell growth factor, various transforming growth factors, platelet derived endothelial cell growth factor, placental growth factor, angiogenin, interleukin-8, or granulocyte colony-stimulating growth factor. These growth factors may be provided to the composition in purified form in concentrations ranging from about $10^{-6}$ to 30 mg/ml, or in equivalent concentrations in an impure or incompletely characterized form, such as in bone, and in cells known to produce angiogenic factors such as endothelial cells, WI-38 cells (human embryonic lung cells), U937 cells (human lymphoma cells), or SK-Hep (human hepatoma cells), and in the supernatant fluid of cell cultures of cells known to produce angiogenic factors such as endothelial cells, WI-38 cells (human embryonic lung cells), U937 cells (human lymphoma cells), or SK-Hep (human hepatoma cells). Alternatively, the production of these factors may be induced by the provision of an angiogenesis-stimulating material such as chitosan or a chitosan derivative (Mori et al., 1997, Biomaterials 18:947). For this purpose and to provide other invention components, chitosan and chitosan derivatives such as imidazolyl chitosan, methylpyrrolidinone chitosan, etc. are useful at concentrations of 1-90%, preferably 35%-65% of the total composition, as a 1-50% (w/v) chitosan gel, preferably 0.5-5%.

The angiogenesis-stimulating nature of a material can be established or confirmed by various assays known in the art, including the incorporation of the material into a slow release Polymer and implanting the polymer into a rabbit cornea (Phillips et al., 1997, Wounds 9:1).

Osteoinductive compounds useful in the compositions of the invention include purified materials known to have these characteristics. Such materials alone or in various combinations may include bone morphogenic proteins (1 to n), transforming growth factors (TGF) (1 to n), insulin growth factors (IGF) (1 to n), platelet derived growth factors (PD-GF), fibroblast growth factors (FGF) (1 to n), tumor necrosis factor (TNF), interleukins (IL) (1 to n), various cytokines, and vitamins such as vitamin D (1-n).

Chitosan has also been shown to promote the differentiation of mesenchymal stem cells into osteoblasts (Klokkevold et al. 1996 J. Periodontology 67:1170), and may thus serve to stimulate at least a part of the mesenchymalosteoblast differentiation process.

Certain complex materials can also conveniently serve as sources of osteoinductive molecules. Such molecules are known to be provided by demineralized bone matrix ("DBM"), which is prepared by grinding cortical bone tissues (generally to 100-500 μm sieved particle size), then treating the ground tissues with hydrochloric acid (generally 0.5 to 1 N). See, e.g., Solheim, 1998, Int. Orthop. 22:335-42. DBM is commercially available, e.g., Grafton® (Osteotech, Eatontown, N.J.); Dynagraft® (GenSci, Irvine, Calif.). It is believed, however, that the acid treatment process used in preparing DBM denatures and/or solubilizes some of the osteogenic molecules present in untreated bone, destroying the osteogenic nature of the denatured molecules or allowing them to leach out of the DBM preparation. Therefore, a preferred source of osteogenic molecules is non-decalcified bone matrix ("NBM"), which is ground cortical bone tissues which are not acid-treated. A combination of non-decalcified bone matrix protein and DBM is also useful in the invention compositions as a source of osteoinductive molecules. The addition of hyaluronic acid may further enhance the osteoinductivity of the mixtures.

The osteoinductive nature of a compound may be determined by known methods such as histomorphometric analysis of trabecular bone formation around a rabbit cranial periosteum implant comprising the putative osteoinductive compound in DBM. See, e.g., Kibblewhite et al., 1993, Growth Factors 9:185.

The scaffolding materials in the compositions of the present invention serve to provide direction and a structure for the development of host neovasculature and osteogenic cells. Materials useful for this purpose include hydroxyapatite-chitosan and sulfated-chitosan composites, materials disclosed in U.S. Pat. No. 5,830,493; 5,563,124; 5,755,792; or 5,711,957, DBM, or, preferably, cancellous bone, chitosan, chitosan-protein fibers, or chitin-protein fibers. Cancellous bone may be obtained from any source, including cadavers. When used as a scaffolding material, the cancellous bone is preferably milled to 0.1-1.5 mm in its longest diameter. Cancellous bone is used in these compositions for its osteoconductive character due to its physical characteristics as a scaffolding material. It is not known to provide any live cells or osteoinductive growth factors. $CaSO_4$, $CaCO_3$, and other calcium salts can also be formed into crystals, either singly or combined with chitosans, to be used as scaffolding materials. The scaffolding material is utilized in the compositions at 10-50%, preferably 20-40%.

Chitosan-protein and chitin-protein fibers are preferably produced by the method described for chitosan-protein fibers in Elgin et al, 1998, Neurological Res. 20:648.

The substance which holds the angiogenesis-stimulating agent and osteogenic molecules and allows the slow release of these components can be any biocompatible compound known to have these properties. The slow release of these factors provides the maximum angiogenic and osteogenic benefit. See, e.g. Tabata et al., 1998, Biomaterials 19:807. Examples of materials useful for this purpose include gelatin hydrogels (Tabata et al., Id.) and alginate-chitosan (Gaserod et al., 1998, Biomaterials 19:1815). As previously discussed, this material, if desired, may also provide a flowable characteristic to the composition. Preferred material to supply these functions is chitosan gel, which may also serve as a material to prevent movement of the composition (see below), as well as an angiogenesis-stimulating agent. Alternatively, the angiogenesis-stimulating agent and/or osteogenic molecules can be encapsulated in microcapsules dispersed in the composition. The microcapsules can be composed of, e.g., chitosan or a mixture of chitosan and alginate (Gaserod et al., Id.), xyloglucan polysaccharide gel (Miyazaki et al., 1998, J. Controlled Release 56:75), or any other biocompatible formulation known in the art. The microcapsules may be dispersed evenly throughout the composition. Alternatively, the microcapsules can be concentrated in an area of the composition where stimulation of angiogenesis or osteogenesis is most useful. An example of such an area is the area adjacent to existing, live bone, where the angiogenesis-stimulating agent would be expected to stimulate the production of neovasculature from the live bone.

The invention compositions further comprise a substance for preventing the composition from moving away from the location where it is placed. This substance is preferably a semi-solid, moldable structure to allow the composition to be formed into the shape needed for the particular application to which the composition is being used. Again, this material can also be flowable, angiogenic, osteoconductive, and/or osteoinductive, providing aspects of other components of the invention compositions. Useful materials for this purpose include alginate, alginate derivatives, gelatin, hydroxyapatite, tricalcium phosphate, calcium carbonate, and hyaluronic acid. Preferred gel-forming materials are chitosan and chitosan derivatives such as imidazolyl chitosan or methylpyrrolidinone chitosan. Combinations of these materials may also be utilized advantageously to create the consistency needed for any particular application. The component proportions of the materials in these combinations may be modified to adjust, e.g., the pH, or the consistency of the composition.

As previously mentioned, certain materials can provide the function of more than one component of the invention composition. In particular, the angiogenic/osteogenic slow release component and the component which prevents the composition from moving can be advantageously combined within one material. Chitosan or chitosan derivatives such as imidazolyl chitosan or methylpyrrolidinone chitosan may provide such a multi-component function. The percentage of chitosan is adjusted in these compositions to provide the desired thickness and flow characteristics of the composition, as well as the desired rate of release of the angiogenic and osteogenic growth factors. As previously discussed, chitosan can also wholly or in part provide the angiogenic stimulation component of the compositions.

The thickness of the gels useful for this invention are known to be affected by other materials present in the composition, particularly calcium-containing materials such as tricalcium phosphate and calcium chloride. For example, the thickness of chitosan gel is known to be affected by the presence of tricalcium phosphate. See U.S. Pat. Nos. 5,563,124; 5,711,957. Also, the thickness of alginate gels for this invention are affected by the presence of calcium chloride as described in example 1 and shown FIGS. 3A and 3B. Since NBM retains the calcium phosphate from the bone matrix, it provides calcium which can combine with the chitosan gel to thicken and harden the gel, particularly in an acidic environment. Therefore, the thickness of chitosan gel used in the invention compositions may be increased by increasing the amount of NBM, or increasing the NBM:DBM ratio, if both materials are used for the osteoinduction component.

Chitosan or chitosan derivatives can also be used alone to stimulate bone growth. In particular the chitosan-based materials can be formed into solid or tubular structures which can be used as supporting, bridging or guiding structures for bone repair. Chitin-based materials may also provide similar functions. These structures can be made, for example, using the glutaraldehyde cross-linking method disclosed in Jameela et al., 1995, Biomaterials 16:769-775. Similar methods can be employed to make other cross-linked chitin or chitosan materials, e.g., those cross-linked with carbodiimide, lysine, and vinyl. Incorporating fibers of these chitin, chitosan or derivatives in multidirectional woven or layered patterns provides further strength. For example, solutions of these compounds can be conformed into desired shapes, (e.g., sheets, rods, columns, tubes, etc.) and solidified by, e.g., drying, curing with vacuum or heat, or addition of salts of minerals (i.e. calcium, sodium). Porous foam-like chitin or chitosan-based materials with a bone-like structure can also be prepared, e.g. by the method disclosed in Thomson et al., 1995, J. Biomaterials Sci. 7:23-38. These solid materials could also be impregnated with chitosan solutions before or after implantation to fill the structure and add adhesiveness and strength.

The compositions are useful in methods where they are applied to sites in humans or other vertebrates where bone formation and growth is desired. Examples of the use of the invention compositions given herein should be considered to be non-limiting.

The invention compositions are useful, for example, at sites with bone defects due to surgery (as occurs, e.g., with the removal of a bone tumor), trauma, or a congenital deficiency (e.g., to correct a cleft palate). Periodontal applications include the use of the compositions to strengthen teeth implants and to repair surgically cut facial bones, e.g., mandibles during plastic surgery.

The invention compositions may be applied as a coating of an allograft or autograft used to fill in the defect, or at the junction of the graft and the native bone (the graft-host interface). Alternatively, the compositions may be applied as a gel or as a rigid, bonelike structure (e.g., comprising a chitosan derivative as previously described), optionally surrounded and/or impregnated with more flowable compositions to fill in undesired gaps. The rigid structure can serve as a bone replacement, providing strength and support until new bone replaces the structure. These rigid structures can, for example, serve as a bone strut, taking the shape of honeycombed tubular or flat structures. The rigid structures can also be formed into strong hollow tubes to be used as bridges. For example, the tube can be filled with a chitosan solution and bridge the two ends of a cylindrical disconnected bone. The rigid structures are also useful for forming an intervertebral fusion or a spinal prosthesis, e.g., after the removal of a disc, to maintain intervertebral spacing.

A bone can also be replicated in the laboratory using morphometric and biometric information, e.g., obtained from the original bone. Utilizing various imaging techniques such as X-rays, CT and MRI scans, holography, densitometry refraction, etc., the structure, density, configuration, contours, strength, etc. of a particular bone (e.g., a femur head or a metacarpal bone) can be replicated using the invention compositions and inserted as a functional composition. See, e.g., Zentner et al., 1996, Angle Orthodontist 66:463; Ko, 1998, J. Neurosurg. 88:777; Katz et al, 1998, Med. Eng. & Physics 20:114; Abe et al., 1998, Neurologia Medico-Chirurgica 38:746. Components of articulated structures such as artificial knees or hips could also be constructed using these compositions. These articulated structures can, for example, comprise rigid bone growth-promoting compositions as described herein, cartilage induced, e.g., by the method disclosed in U.S. Pat. No. 5,837,258, and a capsule, e.g., created by chitosan membranes as disclosed in Chandy et al., 1990, Biomat. Art. Cells, *Art. Org.* 18:1-24 or Rao et al., 1997, J. Blamed. Mat. Res. 34:21-28. Due to the angiogenic, osteoconductive, and osteoinductive nature of the invention compositions, it would be expected that the artificial bone structures made from those compositions would ultimately be replaced with new host bone.

The composition may also be used at bone fractures to accelerate healing, or at the junctions between native bone and implants such as knee or hip replacements to prevent loosening of the prosthesis. In particular, use of the invention compositions on fractures (e.g. of the vertebra, hip, or wrist) may be indicated for patients with osteoporosis, since the angiogenic and osteogenic properties of the compositions would be expected to strengthen osteoporotic bone advantageously.

The composition may be used as a prophylactic treatment to prevent fractures in patients with osteoporosis. In this embodiment, bones which are at risk for fracture in osteoporotic patients are first identified by measuring bone density. Bone density is measured using MRI, X-ray, CT-scan, or any other imaging system known in the art for that purpose. The degree of risk for fracture is then assessed based on the bone density measurement. The bones with the highest risk for fracture are then treated with a composition of the present invention by injecting the composition directly into the bone at points where risk for fracture is highest. A preferred apparatus for performing these injections is that disclosed in Provisional Patent Application Ser. No. 60/132,852 which is herein incorporated by reference. Since the composition must flow through a cannula and into the bone, the composition to be injected must be thinner than compositions which are applied directly to bone defects. An example of a useful composition for this purpose is NBM, 10%; DBM, 10%; cancellous bone, 30%; 2% (w/v) chitosan gel, 50%; 1 mg/ml of a purified vascular endothelial growth factor. Specifically, compositions showing good flow properties may be useful for various applications where the use of a syringe or other similar device is preferred. One example of a useful composition for this purpose is 20% cancellous bone; 20% DBM in 3% alginate. Another example of such a composition with good flow properties is 30% cancellous bone; 10% DBM in 3% alginate. Moreover, another composition with good flow properties is 20.6% (w/w) cancellous bone; 12.4% (w/w) DBM; 0.5% (w/w) alginate; 0.3% (w/w) chitosan; 66.2% (w/w) water. An additional composition showing good flow properties includes 130 mg Hyaluronic acid (HA) solution (1.4% HA solution); 54 mg demineralized bone matrix (DBM); and 130 ng purified vascular endothelial growth factor (VEGF). Another composition with good flow properties is 250 mg of Hyaluronic acid (HA) solution (1.4% sodium hyaluronate); 105 mg demineralized bone matrix (DBM); and 25 ng purified vascular endothelial growth factor (VEGF). Yet another composition with good flow properties is 125 mg Hyaluronic acid (HA) solution (1.4% HA solution); 75 mg of crushed cancellous bone; and 125 ng purified vascular endothelial growth factor (VEGF).

Various formulations of the invention composition may be prepared depending on the particular purpose for its application. An example of a useful composition formulation for this invention is a composition where one or more of the materials is basic fibroblast growth factor, platelet derived endothelial growth factor, or vascular endothelial growth factor present at $10^{-6}$ to 30 mg/ml; the demineralized growth factor is present at 5-30%; the non-decalcified bone matrix is present at 5-30%; the scaffolding material is cancellous bone milled to 0.1-1.5 mm in its longest diameter and is present at 10-40%; and the gel material is a 0.5%-5% (w/v) concentration selected from the group consisting of chitosan, alginate, hyaluronic acid, a mixture of alginate with chitosan, present at 10-80%, or a mixture of hyaluronic acid and chitosan. For example, when the invention composition is utilized to fill in a large defect, a formulation is utilized which provides a relatively large amount of scaffolding to provide a structure which will support the developing vasculature and bone. An example of such a formulation is: cancellous bone, 40-50%, preferably 40%; DBM, 5-30%, preferably 10%; NBM, 5-30%, preferably 10%; 1 mg/ml of a purified vascular endothelial growth factor; 5% (w/v) chitosan gel, 20-50%, preferably 40%. Another example of a relatively friable composition is 50% (v/v) cancellous bone; 10% (v/v) DBM in 3% alginate.

If the invention composition is utilized to stimulate bone formation where a supporting scaffolding is not needed, such as at the site of a fracture, or around an allograft or autograft, a minimal amount of scaffolding is utilized, but a relatively large amount of angiogenic factors may be advantageous to promote rapid fusion at the fracture or graft-host interface. A relatively large amount of gel-forming material may also be advantageous in this situation to assure minimal movement of the composition. An example of such a formulation is: cancellous bone, 0-30%, preferably 10%; DBM, 5-15%, preferably 10%; NBM, 5-15%, preferably 10%; up to 10 mg/ml of a purified vascular endothelial growth factor; 3-10% (w/v) chitosan gel, present at 20-90% of the composition, preferably a 5% gel, present at 70%.

Figure 3A:
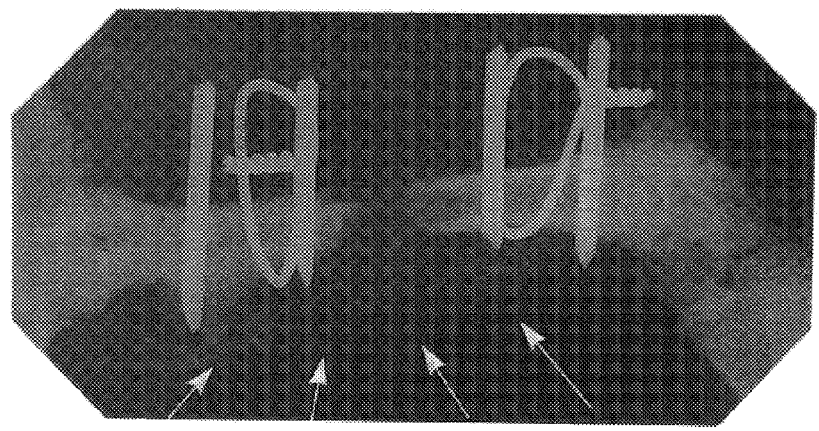
FIG. 3A shows the appearance of bone allograft material in the excipient of alginate without the addition of calcium after implantation of the composition as discussed in Example 1. The image is taken one week after the implantation.
Figure 3B:
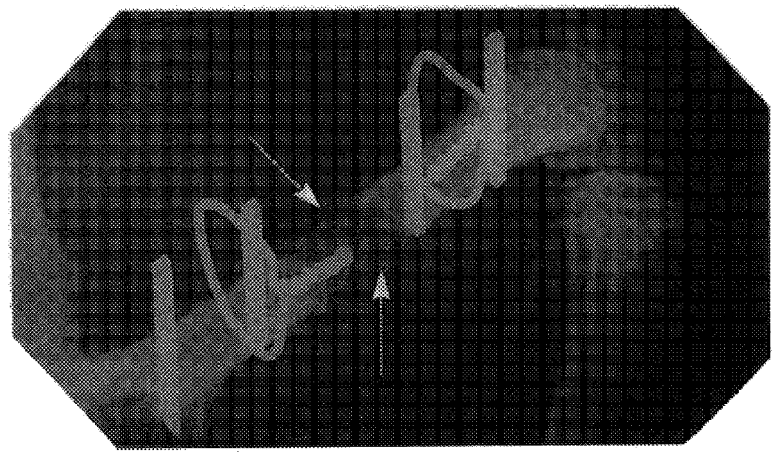
FIG. 3B shows the appearance of bone allograft material in the excipient of alginate with the immediate addition of calcium after implantation of the composition as discussed in Example 1. The image is taken one week after the implantation.

Additionally, other methods to insure the minimal amount of movement of the composition from the site of application may be used. For example, the topical application of calcium to an alginate excipient causes the composition to remain in place, and reduces the flow properties of the composition. The experimental data described below demonstrates the retention properties of a composition using an alginate excipient with the addition of calcium after the composition has been localized to the site of the bone defect. FIG. 3A illustrates the localized appearance of bone allograft material contained in alginate at one week post-implantation when there was no addition of calcium to the alginate mixture. The allograft was observed to migrate from the defect into the hip joint. In contrast, FIG. 3B shows the localized appearance of bone allograft material contained in alginate at one week post-implantation where there was an addition of calcium to the alginate mixture immediately after it was placed in the site of bone defect.

The following examples are intended to illustrate but not to limit the present invention. In light of the detailed description of the invention and the examples presented below, it can be appreciated that the several aspects of the invention are achieved. It is to be understood that the present invention has been described in detail by way of illustration and example in order to acquaint others skilled in the art with the invention, its principles, and its practical application. Particular formulations and processes of the present invention are not limited to the descriptions of specific embodiments presented, but rather the descriptions and examples should be in terms of the claims that follow and their equivalents. While some of the examples and descriptions below include some conclusions about the way the invention may function, the inventor does not intend to be bound by those conclusions and functions, but puts them forth only as possible explanations.

EXAMPLE 1

Surgical Model

This procedure briefly describes the surgical model employed to evaluate the healing potential of bone allograft material in an alginate carrier, following implantation within a clinically significant bone defect. The technique was reproduced from the following reference: Bruder et al., "*Bone Regeneration by Implantation of Purified, Culture Expanded Human Mesenchymal Stem Cells*," J. Orthopaedic Research 16:155162 (1998).

A bilateral surgical model was created to evaluate a novel composition of human allograft bone in an excipient carrier when placed in a clinically significant osseous defect. Such defects fail to undergo intrinsic repair without osteogenic/osteoinductive augmentation.

Figure 1B:
FIG. 1B shows the exposed femur of an athymic nude rat prior to any creation of bone defects in the animal for the study of the bone allograft compositions of this invention as discussed in Example 1.
Figure 1C:
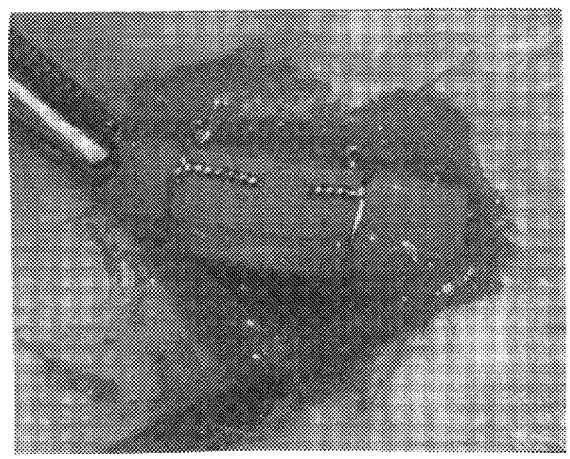
FIG. 1C shows the placement of a fixator plate on the exposed femur of an athymic nude rat prior to the creation of a bone defect in the femur for the study of the bone allograft compositions of this invention as discussed in Example 1.
Figure 2A:
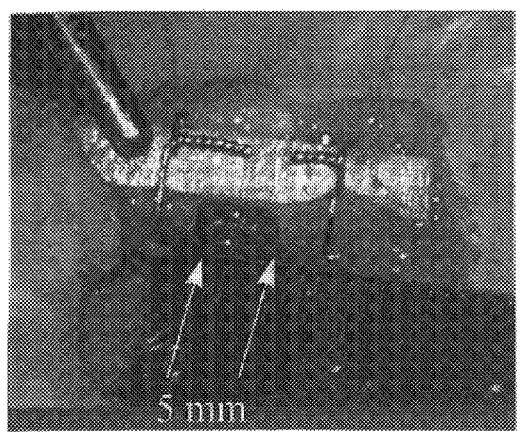
FIG. 2A shows the creation of a bone defect in the exposed femur of an athymic nude rat after placement of the fixator plate in order to study the bone allograft compositions of this invention as discussed in Example 1.
Figure 2B:
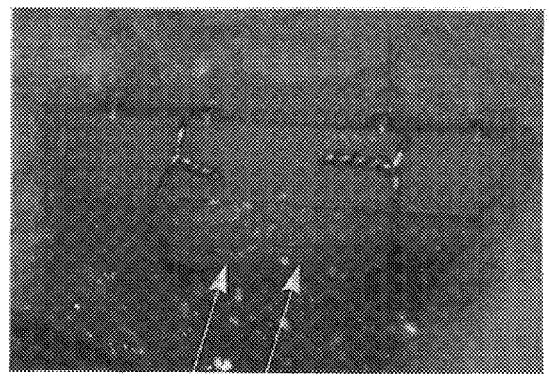
FIG. 2B shows the exposed femur of an athymic nude rat after the implantation of bone allograft material of the present invention subsequent to placement of a fixator plate and the creation of a bone defect in the femur of the rat as discussed in Example 1.

Both femurs of athymic nude rats 12-16 weeks of age (National Cancer Institute, Rnu−/−) were exposed via an anterolateral surgical approach as shown in FIGS. 1A and 1B. A predrilled high density polyethylene fixation plate measuring 4 mm×4 mm×23 mm, with 9 mm pre-drilled center holes (straight) was subsequently attached to each femur by four (4) Kirschner wires and two (2) cerclage wires as shown in FIG. 1C. A 5 mm transverse segment of the central diaphysis, including the adherent periosteum, was removed using a side cutting burr under saline irrigation as shown in FIG. 2B. Excipients used in the current studies consisted either of 3% alginate from various sources or high viscosity hyaluronic acid (Healon GV, Pharmacia/Upjohn). Bone allograft material was held in place via the apposing musculature, and the fascia and skin were closed using 5-0 Ethibond and 5-0 Ethilon sutures, respectively. Animals were euthanized between 1 and 12 weeks for radiographic evaluation of new bone formation. Femurs were collected and fixed in 10% neutral buffered formalin and processed for histologic evaluation upon staining with either saffranin-O/fast green or geimsa.

Figure 5:
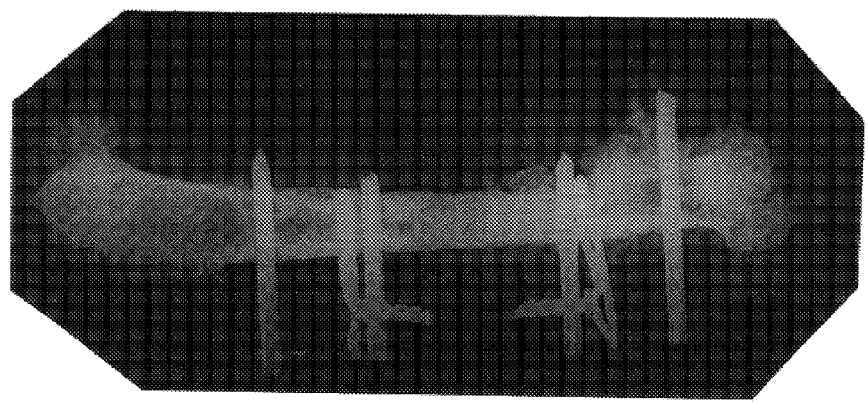
FIG. 5 shows the formation of new bone 12 weeks after the implantation of a bone allograft of the current invention into the femur of an athymic nude rat with a bone defect. The bone allograft composition used for the rat of FIG. 5 is a mixture of demineralized bone matrix (DBM), Hyaluronic acid (HA) and purified vascular endothelial growth factor (VEGF).
Figure 6:
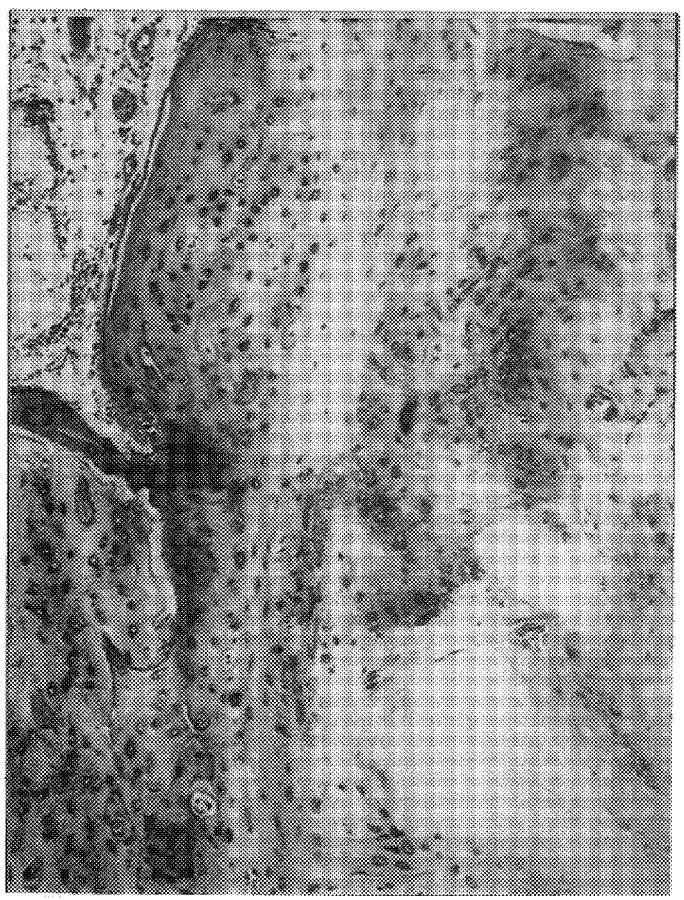
FIG. 6 shows the histologic evaluation of the new bone formation of the athymic nude rat of FIG. 5.

Results:

FIG. 5 illustrates the appearance of bone formation at the site of bone defect after the application of the composition containing demineralized bone matrix (DBM), Hyaluronic acid (HA), and purified vascular endothelial growth factor (VEGF) at 12 weeks. The composition used for the animal of FIG. 5 is 130 mg of HA solution (1.4% sodium hyaluronate), 54 mg of DBM, and 130 ng of VEGF. FIG. 6 is a histologic evaluation of the new bone formation shown in FIG. 5. In FIG. 6 the pink area demonstrates excellent new bone formation.

Comparison of Negative Controls During Model Development

Figure 4A:
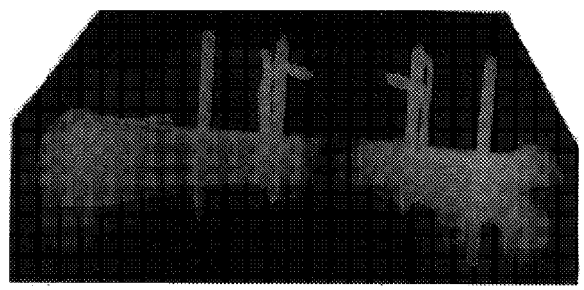
FIG. 4A shows the negative controls for the study of the bone allograft compositions of this invention as discussed in Example 1.
Figure 4B:
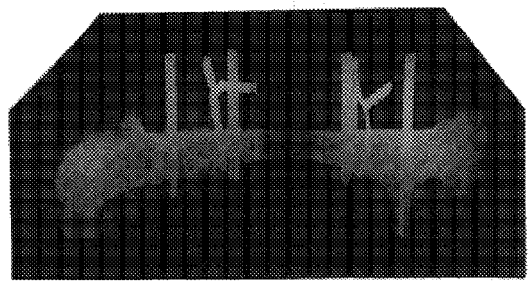
FIG. 4B shows the negative controls for the study of the bone allograft compositions of this invention as discussed in Example 1.

FIG. 4 shows a comparison of the results obtained at 12 weeks postoperatively. Panels A and C represent negative controls in which femoral defects were either left untreated or filled with alginate excipient alone, respectively. Note that there is no bridging of the defect with new bone.

Calcium Augmentation of Alginate Excipient Prevents Migration of Bone Allograft Material Alginate was dissolved in PBS (final concentration 3%) and mixed with bone allograft prior to implantation as described above. Once the defects were filled, calcium chloride solution (50 μl, 5 mM) was applied topically to the alginate/bone material, at which point the excipient material polymerized to form a hardened gel. Identical material in the contralateral limb was left untreated. Animals were sacrificed at 1 and 2 weeks for radiographic evaluation of the implanted bone material, and the tissues were subsequently harvested for histologic evaluation. FIG. 3A illustrates the localized appearance of bone allograft material in alginate without the addition of calcium one (1) week post implantation. The allograft was observed to migrate from the defect into the hip joint where heterotopic ossification occurred within a 12 week period. In contrast, topical application of calcium to the alginate excipient caused the bone allograft to be retained within the defect as shown in FIG. 3B.

Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A composition comprising:
   (a) one or more materials selected from the group consisting of fibroblast growth factors, vascular endothelial growth factors, endothelial cell growth factors, transforming growth factors, chitosan, bone, platelet derived endothelial-growth factors, placental growth factors, angiogenin, interleukin-8, granulocyte colony-stimulating growth factor, and supernatant fluid from a culture of cells known to produce angiogenic factors;
   (b) a material comprising demineralized bone matrix, non-decalcified bone matrix, and hyaluronic acid or a salt thereof; and
   (c) a scaffolding material, wherein the scaffolding material comprises cancellous bone.

2. The composition of claim 1, further comprising:
   (d) a gel material selected from the group consisting of chitosan, imidazolyl chitosan, methylpyrrolidinone chitosan, carbodiimide chitosan, glutaraldehyde chitosan, and a mixture of alginate with chitosan or a chitosan derivative.

3. The composition of claim 2, wherein the gel material is selected from the group consisting of alginate, chitosan, or a mixture of chitosan and alginate.

4. The composition of claim 3, wherein the cancellous bone is milled to 0.1-1.5 mm in its longest diameter and is present at 10-40%; and the gel material is a 2-5% (w/v) concentration selected from the group consisting of chitosan, alginate, or a mixture of alginate with chitosan, present at 35-80%.

5. The composition of claim 3, wherein the cancellous bone is present at 10%; and the gel material is a 3% (w/v) concentration of alginate, or a mixture of alginate with chitosan.

6. The composition of claim 3, wherein the cancellous bone is present at 20%; and the gel material is a 3% (w/v) concentration of alginate, or a mixture of alginate with chitosan.

7. The composition of claim 3, wherein the cancellous bone is present at 30%; and the gel material is a 3% (w/v) concentration of alginate, or a mixture of alginate with chitosan.

8. The composition of claim 3, wherein the cancellous bone is present at 15-25% (w/w); and the gel material is a 3% (w/v) concentration of alginate, or a mixture of alginate with chitosan.

9. The composition of claim 1, wherein one or more of the said one or more materials is basic fibroblast growth factor, a vascular endothelial growth factor, platelet derived endothelial growth factor, bone, or supernatant fluid from a culture of cells known to produce angiogenic factors.

10. The composition of claim 1, wherein said demineralized bone matrix, non-decalcified bone matrix and cancellous bone consist essentially of bone allograft material.

11. The method of claim 10, wherein said cancellous bone is milled to 0.1-1.5 mm in its longest diameter.

12. The composition of claim 1, wherein the hyaluronic acid or salt thereof is present at a 0.5%-5% (w/v) gel concentration.

13. The composition of claim 1, wherein said cancellous bone is milled to 0.1-1.5 mm in its longest diameter.

14. The method of claim 13, wherein said demineralized bone matrix, non-decalcified bone matrix and cancellous bone consist essentially of bone allograft material.

15. The method of claim 13, wherein the hyaluronic acid or salt thereof is present as a 0.5%-5% (w/v) gel concentration.

* * * * *